United States Patent [19]

Pang

[11] Patent Number: 5,011,686

[45] Date of Patent: Apr. 30, 1991

[54] THROMBUS SPECIFIC CONJUGATES

[75] Inventor: Roy H. L. Pang, Medway, Mass.

[73] Assignee: Creative Biomolecules, Inc., Hopkinton, Mass.

[21] Appl. No.: 437,769

[22] Filed: Nov. 15, 1989

Related U.S. Application Data

[63] Continuation of Ser. No. 99,242, Sep. 21, 1987, abandoned.

[51] Int. Cl.$^5$ ............... A61K 37/02; A61K 37/48; A61K 37/547
[52] U.S. Cl. .................. 424/94.1; 424/94.63; 424/94.64; 435/13; 435/183; 435/215; 435/216; 514/2; 514/12; 530/300; 530/324; 530/345; 530/350
[58] Field of Search ............ 530/300, 324, 345, 350; 435/7, 13, 183, 215, 216; 514/2, 12; 424/94.1, 94.63, 94.64

[56] References Cited

U.S. PATENT DOCUMENTS

| | | | |
|---|---|---|---|
| 4,312,942 | 1/1982 | Blobel et al. | 435/7 |
| 4,478,914 | 10/1984 | Giese | 435/7 |
| 4,560,556 | 12/1985 | Kagitani et al. | 530/829 |
| 4,578,079 | 3/1986 | Ruoslahti et al. | 530/330 |

OTHER PUBLICATIONS

Colbert et al., Journal of Biological Response Modifiers, vol. 3, pp. 255-259 (1984).
Kerenyi et al., Biological Abstr., vol. 81, No. 11099 (1/15/86).
Crea et al., Chem. Abstr., vol. 109, No. 184bm (1988).
Doran et al., Infection and Immunity, vol. 33, No. 3, pp. 683-689 (9/1981).
Rudinger, Peptide Hormones, Parsons (Ed.), U. Parts Press, pp. 1-7 (1976).
Morii et al., The Journal of Biological Chemistry, pp. 12749-12752, (1983).
Phillips, Annals of Neurology, vol. 25, No. 3, pp. 281-285 (3/1989).

Primary Examiner—John Doll
Assistant Examiner—Christina Chan
Attorney, Agent, or Firm—Lahive & Cockfield

[57] ABSTRACT

Disclosed is a method of targeting reagents to the locus of a clot, and a family of substances that have affinity for fibrin. The method and substances exploit the discovery that the binding sites on protein A from *Staphylococcus aureus* have a significant affinity for fibrin. These fragments, analogs thereof, and oligomers of the fragments or analogs, may be attached to fibrinolytic enzymes, remotely detectable radiation emitting moieties, or healing agents to produce reagents which have affinity for the site of a wound or intravascular clot where fibrin has been deposited. Constructs comprising repeats of truncated analogs of the binding domain have low affinity for circulating immunoglobulin and high affinity for fibrin.

11 Claims, 11 Drawing Sheets

```
START         10          20          30
ATGGCTGACAACAAATTCAACAAGGAACAGCAGAAC
MetAlaAspAsnLysPheAsnLysGluGlnGlnAsn
 M   A   D   N   K   F   N   K   E   Q   Q   N 40          50          60
GCGTTCTACGAGATCTTGCACCTGCCGAACCTGAAC
AlaPheTyrGluIleLeuHisLeuProAsnLeuAsn
 A   F   Y   E   I   L   H   L   P   N   L   N 70          80          90         100
GAAGAGCAGCGTAACGGCTTCATCCAAAGCTTGAAA
GluGluGlnArgAsnGlyPheIleGlnSerLeuLys
 E   E   Q   R   N   G   F   I   Q   S   L   K 110         120         130          1
CACGACCCGTCTCAGAGCGCTAACCTGCTGGCAGAG
AspAspProSerGlnSerAlaAsnLeuLeuAlaGlu
 D   D   P   S   Q   S   A   N   L   L   A   E 40          150         160         170
GCCAAGAAACTGAACGACGCTCAGGCGCCGAAG
AlaLysLysLeuAsnAspAlaGlnAlaProLys
 A   K   K   L   N   D   A   Q   A   P   K
```

*FIG. 1A*

FB-58   ADNKFNKEQQNAFYEILHLPNLNEEQRNGFIQSLKDDPSQSANLLAEAKKLNDAQAPK

FB-TF           EQQNAFYEILHLPNLNEEQRNGFIQSLKDDPSQSANLLAEAKKLNDAQAPK

FB-36   ADNKFNKEQQNAFYEILHLPNLNEEQRNGFIQSLKD

FB-29           EQQNAFYEILHLPNLNEEQRNGFIQSLKD

FB-40           EQQNAFYEILHLPNLNEEQRNGFIQSLKDDPSQSANLLAE

FB-47   ADNKFNKEQQNAFYEILHLPNLNEEQRNGFIQSLKDDPSQSANLLAE

```
  1        10         20         30         40         50
GAATTCATGGCTGACAACAAATTCAACAAGGAACAGCAGAACGCGTTCTAC
GluPheMetAlaAspAsnLysPheAsnLysGluGlnGlnAsnAlaPheTyr
EcoRI                                          MluI
                                               XmnI 60         70         80         90        100
GAGATCTTGCACCTGCCGAACCTGAACGAAGAGCAGCGTAACGGCTTCATC
GluIleLeuHisLeuProAsnLeuAsnGluGluGlnArgAsnGlyPheIle
 BglII                      EarI- 110        120        130        140        150
CAAAGCTTGAAAGACGACCCGTCTCAGAGCGCTAACCTGCTGGCAGAGGCC
GlnSerLeuLysAspAspProSerGlnSerAlaAsnLeuLeuAlaGluAla
  HindIII                 Eco47III 160        170        180        190        200
AAGAAACTGAACGACGCTCAGGCGCCGAAGGCTGACAACAAATTCAACAAG
LysLysLeuAsnAspAlaGlnAlaProLysAlaAspAsnLysPheAsnLys
                              EheI
                              NarI 210        220        230        240        250
GAACAGCAGAACGCGTTCTACGAGATCTTGCACCTGCCGAACCTGAACGAA
GluGlnGlnAsnAlaPheTyrGluIleLeuHisLeuProAsnLeuAsnGlu
              MluI     BglII                     Ear
              XmnI 260        270        280        290        300
GAGCAGCGTAACGGCTTCATCCAAAGCTTGAAAGACGACCCGTCTCAGAGC
GluGlnArgAsnGlyPheIleGlnSerLeuLysAspAspProSerGlnSer
I-                       HindIII                 Eco 310        320        330        340        350
GCTAACCTGCTGGCAGAGGCCAAGAAACTGAACGACGCTCAGGCGCCGAAG
AlaAsnLeuLeuAlaGluAlaLysLysLeuAsnAspAlaGlnAlaProLys
47III                                       EheI EarI-
                                            NarI 360        370        380        390        400       4
AGTAAACCGTCTAGCCCGCCGGAGGAGCTCAAGTTCCAGTGTGGCCAGAAG
SerLysProSerSerProProGluGluLeuLysPheGlnCysGlyGlnLys
                          SacI                MscI 10       420        430        440        450        46
ACCCTGCGTCCGCGGTTCAAGATCATTGGCGGTGAGTTCACTACGATCGAG
ThrLeuArgProArgPheLysIleIleGlyGlyGluPheThrThrIleGlu
            SacII                              PvuI
```

*FIG. 3A*

```
   0        470       480       490       500       510
AACCAGCCATGGTTCGCTGCAATCTATCGTCGCCATCGTGGTGGGTCCGTC
AsnGlnProTrpPheAlaAlaIleTyrArgArgHisArgGlyGlySerVal
     NcoI                          BstXI 520       530       540       550       560
ACCTACGTTTGTGGTGGAAGCTTGATCAGCCCTTGTTGGGTCATCAGCGCT
ThrTyrValCysGlyGlySerLeuIleSerProCysTrpValIleSerAla
                  HindIII                      Eco47I
                BclI 570       580       590       600       610
ACTCACTGCTTCATCGATTATCCGAAGAAAGAGGATTACATTGTTTACCTC
ThrHisCysPheIleAspTyrProLysLysGluAspTyrIleValTyrLeu
II           ClaI 620       630       640       650       660
GGGCGTTCTCGTCTGAACAGCAATACACAGGGTGAGATGAAATTCGAACTG
GlyArgSerArgLeuAsnSerAsnThrGlnGlyGluMetLysPheGluVal
                         DraIII              AsuII
                                              BstBI 670       680       690       700       710
GAGAACCTAATATTGCATAAGGACTACTCGGCCGATACTCTGGCTCATCAC
GluAsnLeuIleLeuHisLysAspTyrSerAlaAspThrLeuAlaHisHis
       SspI                 EagI
                            XmaIII 720       730       740       750       760
AATGATATCGCTCTGCTGAAGATACGTAGTAAGGAGGGTCGTTGTGCTCAG
AsnAspIleAlaLeuLeuLysIleArgSerLysGluGlyArgCysAlaGln
    EcoRV                SnaBI                 EspI 770       780       790       800       810
CCGTCTCGCACTATTCAGACCATATGCCTGCCGTCTATGTACAATGATCCG
ProSerArgThrIleGlnThrIleCysLeuProSerMetTyrAsnAspPro
                           NdeI 820       830       840       850       860
CAGTTCGGTACCAGTTGTGAGATCACTGGTTTCGGTAAAGAGAACAGTACT
GlnPheGlyThrSerCysGluIleThrGlyPheGlyLysGluAsnSerThr
     KpnI                                       ScaI 870       880       890       900       910     9
GATTACCTGCTGTATCCGGAGCAGCTTAAGATGACTGTGGTTAAACTGATC
AspTyrLeuLeuTyrProGluGlnLeuLysMetThrValValLysLeuIle
            BspEI        AflII
```

FIG. 3B

```
     20        930       940       950       960        97
TCTCATCGTGAATGCCAACAGCCGCATTACTATGGCTCGGAGGTTACCACT
SerHisArgGluCysGlnGlnProHisTyrTyrGlySerGluValThrThr
                                              BstEII 0        980       990      1000      1010      1020
AAGATGCTGTGTGCCGCAGATCCGCAGTGGAAGACGGATAGCTGCCAAGGC
LysMetLeuCysAlaAlaAspProGlnTrpLysThrAspSerCysGlnGly 1030      1040      1050      1060      1070
GATAGTCAACAGCCACTAGTTTGCTCCCTGCAAGGTCGTATGACTCTGACC
AspSerGlnGlnProLeuValCysSerLeuGlnGlyArgMetThrLeuThr
                 SpeI 1080      1090      1100      1110      1120
GGTATTGTTTCTTGGGGTCGTGGTTGTGCACTGAAGGATAAACCGGGTGTT
GlyIleValSerTrpGlyArgGlyCysAlaLeuLysAspLysProGlyVal
                                 ApaLI 1130      1140      1150      1160      1170
TACACGCGTGTCTCCCACTTCCTGCCGCAGATACGTAGTCATACTAAGGAA
TyrThrArgValSerHisPheLeuProGlnIleArgSerHisThrLysGlu
   MluI                              SnaBI         Ear 1180      1190      1200
GAGAATGGGCTAGCTCTGTAACTGCAG
GluAsnGlyLeuAlaLeu*oc
I-         NheI         PstI
```

```
  1         10         20         30         40         50
GAATTCATGGCTGACAACAAATTCAACAAGGAACAGCAGAACGCGTTCTAC
      MetAlaAspAsnLysPheAsnLysGluGlnGlnAsnAlaPheTyr
EcoRI                                       MluI
                                            XmnI 60         70         80         90        100
GAGATCTTGCACCTGCCGAACCTGAACGAAGAGCAGCGTAACGGCTTCATC
GluIleLeuHisLeuProAsnLeuAsnGluGluGlnArgAsnGlyPheIle
 BglII 110        120        130        140        150
CAAAGCTTGAAAGACGACCCGTCTCAGAGCGCTAACCTGCTGGCAGAGGCC
GlnSerLeuLysAspAspProSerGlnSerAlaAsnLeuLeuAlaGluAla
   HindIII                              BspMI+

160        170        180        190        200
AAGAAACTGAACGACGCTCAGGCGCCGAAGGCTGACAACAAATTCAACAAG
LysLysLeuAsnAspAlaGlnAlaProLysAlaAspAsnLysPheAsnLys
                              NarI 210        220        230        240        250
GAACAGCAGAACGCGTTCTACGAGATCTTGCACCTGCCGAACCTGAACGAA
GluGlnGlnAsnAlaPheTyrGluIleLeuHisLeuProAsnLeuAsnGlu
              MluI        BglII
              XmnI 260        270        280        290        300
GAGCAGCGTAACGGCTTCATCCAAAGCTTGAAAGACGACCCGTCTCAGAGC
GluGlnArgAsnGlyPheIleGlnSerLeuLysAspAspProSerGlnSer
                          HindIII 310        320        330        340        350
GCTAACCTGCTGGCAGAGGCCAAGAAACTGAACGACGCTCAGGCGCCGAAG
AlaAsnLeuLeuAlaGluAlaLysLysLeuAsnAspAlaGlnAlaProLys
    BspMI+                                  NarI 360        370        380        390        400        4
ATTGCTGGACCTGAGTGGCTGCTAGACCGTCCATCTGTCAACAACACCCAA
IleAlaGlyProGluTrpLeuLeuAspArgProSerValAsnAsnSerGln
       AvaII                            HincII 10        420        430        440        450         46
TTAGTTGTTAGCGTTGCTGGTACTGTTGAGGGGACGAATCAAGACATTAGT
LeuValValSerValAlaGlyThrValGluGlyThrAsnGlnAspIleSer 0         470        480        490        500        510
CTTAAATTTTTTGAAATCGATCTAACATCACGACCTGCTCATGGAGGAAAG
LeuLysPhePheGluIleAspLeuThrSerArgProAlaHisGlyGlyLys
                ClaI                    BspMI+
```

FIG. 5A

```
        520         530         540         550         560
ACAGAGCAAGGCTTAAGTCCAAAATCAAAACCATTTGCTACTGATAGTGGC
ThrGluGlnGlyLeuSerProLysSerLysProPheAlaThrAspSerGly
                AflII 570         580         590         600         610
GCGATGTCACATAAACTTGAGAAAGCTGACTTACTAAAGGCTATTCAAGAA
AlaMetSerHisLysLeuGluLysAlaAspLeuLeuLysAlaIleGlnGlu 620         630         640         650         660
CAATTGATCGCTAACGTCCACAGTAACGACGACTACTTTGAGGTCATTGAT
GlnLeuIleAlaAsnValHisSerAsnAspAspTyrPheGluValIleAsp 670         680         690         700         710
TTTGCAAGCGATGCAACCATTACTGATCGAAACGGCAAGGTCTACTTTGCT
PheAlaSerAspAlaThrIleThrAspArgAsnGlyLysValTyrPheAla
                                              AccI 720         730         740         750         760
GACAAAGATGGTTCGGTAACCTTGCCGACCCAACCTGTCCAAGAATTTTTG
AspLysAspGlySerValThrLeuProThrGlnProValGlnGluPheLeu
              BstEII                                E 770         780         790         800         810
CTAAGCGGACATGTGCGCGTTAGACCATATAAAGAAAAACCAATACAAAAC
LeuSerGlyHisValArgValArgProTyrLysGluLysProIleGlnAsn
spI 820         830         840         850         860
CAAGCGAAATCTGTTGATGTGGAATATACTGTACAGTTTACTCCCTTAAAC
GlnAlaLysSerValAspValGluTyrThrValGlnPheThrProLeuAsn 870         880         890         900         910   9
CCTGATGACGATTTCAGACCAGGTCTCAAGATACTAAGCTATTGAAAACA
ProAspAspAspPheArgProGlyLeuLysAspThrLysLeuLeuLysThr
                                Tth111I 20          930         940         950         960         97
CTAGCTATCGGTGACACCATCACATCTCAAGAATTACTAGCTCAAGCACAA
LeuAlaIleGlyAspThrIleThrSerGlnGluLeuLeuAlaGlnAlaGln 0           980         990         1000        1010        1020
AGCATTTTAAACAAAAACCACCCAGGCTATACGATTTATGAACGTGACTCC
SerIleLeuAsnLysAsnHisProGlyTyrThrIleTyrGluArgAspSer
     DraI 1030        1040        1050        1060        1070
TCAATCGTCACTCATGACAATGACATTTTCCGTACGATTTTACCAATGGAT
SerIleValThrHisAspAsnAspIlePheArgThrIleLeuProMetAsp
```

*FIG. 5B*

```
     1080      1090      1100      1110      1120
CAAGAGTTTACTTACCGTGTTAAAAATCGGGAACAAGCTTATAGGATCAAT
GlnGluPheThrTyrArgValLysAsnArgGluGlnAlaTyrArgIleAsn
                                  HindIII 1130      1140      1150      1160      1170
AAAAAATCTGGTCTGAATGAAGAAATAAACAACACTGACCTGATCTCTGAG
LysLysSerGlyLeuAsnGluGluIleAsnAsnThrAspLeuIleSerGlu 1180      1190      1200      1210      1220
AAATATTACGTCCTTAAAAAGGGGAAAAGCCGTATGATCCCTTTGATCGC
LysTyrTyrValLeuLysLysGlyGluLysProTyrAspProPheAspArg
 SspI 1230      1240      1250      1260      1270
AGTCACTTGAAACTGTTCACCATCAAATACGTTGATGTCGATACCAACGAA
SerHisLeuLysLeuPheThrIleLysTyrValAspValAspThrAsnGlu
     XmnI 1280      1290      1300      1310      1320
TTGCTAAAAAGTGAGCAGCTCTTAACAGCTAGCGAACGTAACTTAGACTTC
LeuLeuLysSerGluGlnLeuLeuThrAlaSerGluArgAsnLeuAspPhe
                           NheI 1330      1340      1350      1360      1370     1
AGAGATTTATACGATCCTCGTGATAAGGCTAAACTACTCTACAACAATCTC
ArgAspLeuTyrAspProArgAspLysAlaLysLeuLeuTyrAsnAsnLeu 380       1390      1400      1410      1420     14
GATGCTTTTGGTATTATGGACTATACCTTAACTGGAAAAGTAGAGGATAAT
AspAlaPheGlyIleMetAspTyrThrLeuThrGlyLysValGluAspAsn 30       1440      1450      1460      1470     148
CACGATGACACCAACCGTATCATAACCGTTTATATGGGCAAGCGACCCGAA
HisAspAspThrAsnArgIleIleThrValTyrMetGlyLysArgProGlu 0        1490      1500      1510      1520     1530
GGAGAGAATGCTAGCTATCATTTAGCCTATGATAAAGATCGTTATACCGAA
GlyGluAsnAlaSerTyrHisLeuAlaTyrAspLysAspArgTyrThrGlu
      BsmI+
      NheI 1540      1550      1560      1570      1580
GAAGAACGAGAAGTTTACAGCTACCTGCGTTATACAGGGACACCTATACCT
GluGluArgGluValTyrSerTyrLeuArgTyrThrGlyThrProIlePro
                   BspMI+

1590      1600      1610      1620      1630
GATAACCCTAACGACAAATAACCACGGTCTTCTAAAACGATGAGATTAACT
AspAsnProAsnAspLys*oc
```

*FIG. 5C*

```
      1640      1650      1660      1670      1680
GACAAAAAAAGCAAGCAACATGCTATTCAACAGTTGCTTGCTTTTTTCTAA 1690      1700      1710     ·1720      1730
CCTCTTCTAGGACATTTCGTGTCTAAAATAATCGTAACTGGTCCATCATTG
                                          AvaII 1740      1750      1760      1770      1780
ATGAGACTAACCTGCATATCTGCCCCAAAAACGCCACGTCAACTGGCACAA
        BspMI+                        HincII 1790      1800      1810      1820      1830
AATCAGTTGTAGAGATGCCAATTGTTCATTAAAGCGATCATAAAACTGGCT
                                              NheI 1840      1850      1860      1870      1880     1
AGCCATATCAGCTTTGCAGCAGCTCCTGTAAAGGCTGGGCGATTTCCCTTT 890       1900      1910      1920      1930      19
TTGGTGTCAGATAAAGGGTAAATTGCGACACAGATAAGATACTACCCTTGA 40      1950      1960      1970      1980       199
TGTCTTGGATAGACTGATTCATCTTGCCATCAGCATCTGAAAAAATGCGAT 0       2000      2010      2020      2030
GTTGACTATTTTTGCACAGCGTAAGCCAAAATCTTCTGCAG
HincII                                 PstI
```

THROMBUS SPECIFIC CONJUGATES

This application is a continuation of application Ser. No. 099,242 filed Sept. 21, 1987, now abandoned.

BACKGROUND OF THE INVENTION

This invention relates to a family of reagents which have affinity for fibrin. The reagents comprise a moiety defining a fibrin binding site linked to a biologically active domain having fibrinolytic or therapeutic activity, or a property which enables imaging of intravascular thrombi. More particularly, the invention relates to a method of imparting to injectable agents an affinity for fibrin.

Spontaneous formation of blood clots and their subsequent dissolution by the coagulation and fibrinolytic systems are important functions in the body's natural healing process. However, the formation of intravascular clots is the cause of many diseased conditions such as deep vein thrombosis, stroke, and myocardial infarction. Intravascular anticoagulant therapy has been used successfully to prevent the formation of clots, but treatment options are limited after a thrombus has formed and is lodged within the body.

Currently, there are a number of drugs under development or in clinical testing which may be useful as intravascular fibrinolytic agents. For example, recombinant tPA, urokinase, prourokinase, and streptokinase have been, now are, or will soon be offered commercially for this purpose. TPA is a serine protease which catalyzes the conversion of the inactive protein plasminogen to plasmin. Plasmin then dissolves the fibrin clot. TPA can bind specifically to fibrin and its proteolytic action is thereby at least theoretically limited to the location of the clot. Prourokinase is fibrin selective. Urokinase and streptokinase, on the other hand, do not exhibit this fibrin binding specificity or selectivity. Administration of these reagents can cause significant peripheral bleeding.

While the successful management of these diseased states will be aided when development of the therapeutic agents discussed above is complete, there is nevertheless a need for therapeutic and diagnostic agents which selectively bind to intravascular thrombi. In addition to fibrinolytic agents, reagents useful for imaging clots which would permit the physician to determine their precise location would be valuable. Also, analgesic and therapeutic agents which could be targeted to the sight of a wound where clotting naturally occurs would have clinical value.

Monoclonal antibodies potentially can provide a moiety which specifically binds to an epitope of fibrin or another constituent of a thrombus. See Haber et al, EPO 187,658. The state of the art is such that coupling biochemically active agents to an antibody so that the agent retains its biological activity and the antibody retains its specificity can be achieved readily. A monoclonal antibody tagged, for example, with a gamma emitting radioactive atom, theoretically could be administered to image a thrombus. See Childs et al, J. Nucl. Med. V. 26, No. 3, pp 293, and Rosebrough, Radiology, 1985, 156:515. However, administration of murine and rat monoclonals to humans has potentially serious immunological side effects. Monoclonals of human origin which might be less antigenic are notoriously difficult to produce.

U.S. Pat. No. 4,312,942 discloses a reagent for the detection of fission products of fibrinogen and/or fibrin which comprises, as an active component, a suspension of a clumping factor-positive microorganism extract from *Staphylococcus aureus*, especially strain K807. It is known that Protein A from *Staphylococcus aureus* binds with the $F_c$ fragment of human immunoglobulin (see, e.g., U.S. Pat. No. 4,478,914). Howiger et al, in Ann NY Acad. Sci., 1983, Vol. 408, pgs. 521–535, disclose that fibrinogen interacts with several types of cells including *Staphylococcus aureus*. The interaction is said to involve the binding of fibrinogen to specific cell receptors resulting in clumping of the bacteria. This article reviews research directed to the interaction of fibrinogen with procaryotic cells. Kolawole, in J. Hyg., (Camb.) 1984, Vol. 92, Pgs. 183–192, disclose the results of a study of the mechanism by which *Staphylococcus aureus* strains assume increased resistance to polymorph bactericidins if grown in plasma. The author reports that one of the mechanisms of acquiring resistance appears to involve an interaction between *Staphylococcus aureus* and fibrinogen, resulting in the deposition of fibrin or fibrin derivatives on the bacterial surface. The author speculates that the presence of fibrin on the cell surface could result from interactions between plasma proteins and *Staphylococcus aureus* factors such as clumping factor, free coagulase, or protein A, citing Forsgren and Sjoquist, *Protein A from Staphylococcus aureus*, J. Immuno. V., 97, pgs. 822–827.

Also, various radioactive atoms have been coupled with tPA, Fragment $E_1$ from the plasmic digestion of cross-linked fibrin, and human platelets for use as imaging agents. See, e.g., Knight et al, Radiology, 1985, V. 156, pp 509–514; Knight et al, The Journal of Nuclear Medicine, Vol. 19, No. 8, p 891; and Krohn et al, Seminars in Nuclear Medicine, Vol 8, No. 3, July, 1977. In these studies I-123, In-111, Br-77, Tc-99, and I-131 have been linked to materials having fibrin affinity by various conventional methods.

SUMMARY OF THE INVENTION

It has now been discovered that the binding domains of *Staphylococcus aureus* derived protein A, especially the FB domain, analogs thereof, and oligomers of the native fragments or their analogs, have selective affinity for fibrin. These proteins have only low affinity for fibrinogen, fibrin's soluble precursor, and therefore may be used intravascularly to target fibrin present at the site of a clot.

The native amino acid sequence of the FB fragment and the DNA encoding the sequence are set forth in FIG. 1. As is evident from the Figure, the sequence is cysteine-free and comprises 58 amino acid residues beginning with Ala and ending with Lys. In other binding domains of protein A, e.g., the FA, FC, FD, and FE domains, much of the sequence is conserved. This native FB and the other binding domains have significant affinity for fibrin and for the $F_c$ portion of immunoglobulin. FB has an affinity constant of about $1.4 \times 10^7 M^{-1}$ for fibrin. FB and the other binding domains have an affinity constant of about $5 \times 10^7 M^{-1}$ for the Fc portion of circulating immunoglobulin. Protein constructs having higher affinity for fibrin and lower affinity for Fc can be produced by forming oligomers, i.e., linking truncated or otherwise altered analogs of these binding domains, which individually exhibit reduced binding for Fc (and typically also for fibrin). If the affinity constant for fibrin of the analog is Ka, then the constant for the oligomer is on the order of $(Ka)^n$, where n is the number of repeats in the oligomer, and does not exceed 10. Thus, for example, a trimer, composed of analogs each of which have a Ka for fibrin and for Fc of about $10^3 M^{-1}$, can have an affinity for fibrin as great as about $10^9 M^{-1}$. Alternatively, the native binding domain may be modified as disclosed herein empirically by amino acid substitution to retain high fibrin affinity and to reduce Fc affinity.

The foregoing discoveries enable the preparation of a family of fibrin-specific reagents useful, for example, in determining the location of an intravascular clot, delivering a fibrinolytic agent to the clot, or delivering various analgesic or therapeutic agents to the site of a wound where a clot has formed.

Broadly, the invention comprises a method for imparting to an injectable agent, e.g., an imaging, fibrinolytic, therapeutic, or analgesic agent, an affinity for fibrin whereby the agent can be targeted to the site of a wound or intravascular clot. The method comprises the step of linking to the agent a protein constituting a binding domain of protein A, preferably the FB fragment, an analog thereof having affinity for fibrin, or an oligomer of the binding domain protein or the analog, to produce a conjugate which retains both fibrin affinity and the bioproperties of the injectable agent.

Thus, in one aspect, the invention comprises a reagent for determining the location of the thrombus in the circulatory system of an animal. The reagent comprises a conjugate of the formula $(F)_n$-L-I where F is the FB or another fragment of protein A or an analog thereof having affinity for fibrin, n is an integer, preferably between about 1-10 and more preferably two to five, I is remotely detectable moiety such as a radiation emitting, e.g., gamma emitting, radioactive atom, and L is a covalent bond or a linker covalently attaching $(F)_n$ and I. Thus, either the binding fragment alone, oligomers thereof, analogs thereof which retain affinity for fibrin, or oligomers of the analogs, may be linked through a short polypeptide or a single bond to various remotely detectable moieties, e.g., a lysine rich polypeptide sequence coupled to a radioactive atom.

In another embodiment of the invention, the constructs having fibrin affinity may be linked to an enzymatically active fragment of urokinase, streptokinase, or plasminogen activator to produce a synthetic fibrinolytic drug. It is also contemplated that various therapeutic or analgesic agents be coupled to the fragment for targeted delivery to the site of a wound.

The preferred methods of manufacturing such conjugates involve the production of synthetic DNA, or the linking of DNAs from various sources, which encode at least the protein backbone of the conjugate, transfecting the DNA into a suitable host, and expressing the conjugates as a fusion protein which is collected and purified. Subsequently, if necessary, non protein substances may be linked to the protein. For example, a radioactive atom, a therapeutic drug, or an analgesic drug may be linked to the protein using conventional methods.

It is accordingly an object of the invention to provide a family of conjugates useful in vivo or in vitro which have selective affinity for fibrin. Another object is to produce such conjugates comprising protein having only minimal, acceptable immunogenicity. Still another object is to provide methods for producing biosynthetic, bioactive Polypeptides which have selective affinity for fibrin.

These and other objects and features of the invention will be apparent from the following description, drawing, and claims.

DESCRIPTION

The invention is based on the discovery that the binding domains of protein A, particularly the FB fragment depicted in FIG. 1, has high affinity for fibrin and far lower affinity for other human and animal proteins such as fibrinogen and bovine serum albumin. Surprisingly, the protein A binding domains have a low affinity for solubilized fibrinogen, as demonstrated in inhibition assays, but a high affinity for the closely related material fibrin.

As will be appreciated by those skilled in the art, the affinity of a protein for fibrin or any other target does not depend on precise duplication of the amino acid sequence of the native material. Accordingly, many other specific protein structures comprising sequences having deletions, additions, and substitutions of specific amino acids or amino acid regions will retain fibrin binding activity.

Figure 1A:
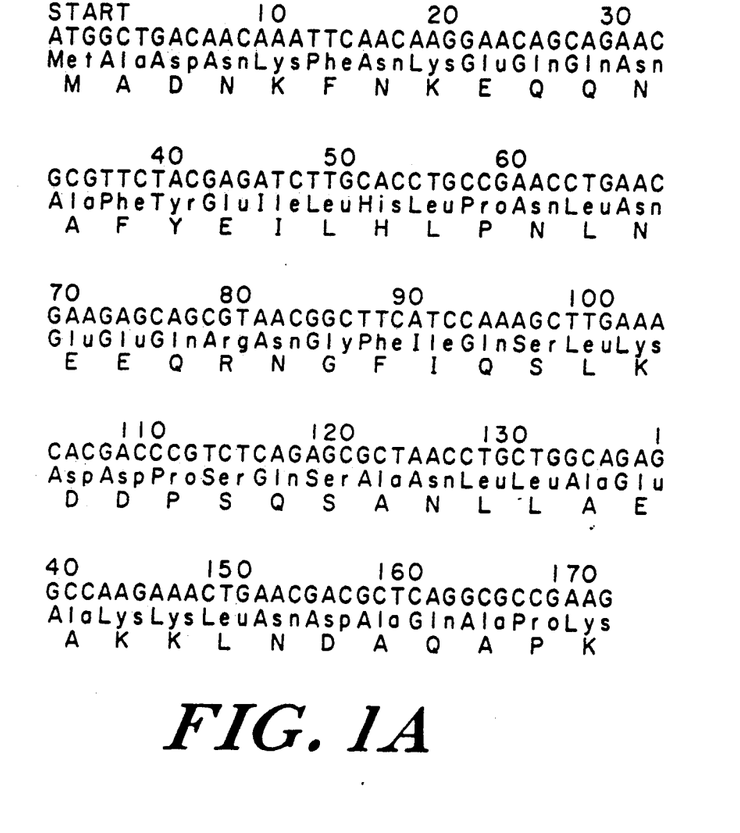
FIG. 1A is the full length DNA sequence encoding the native FB fragment of protein A from *Staphylococcus aureus* together with its amino acid sequence shown in three letter and single letter standard code.
Figure 1B:
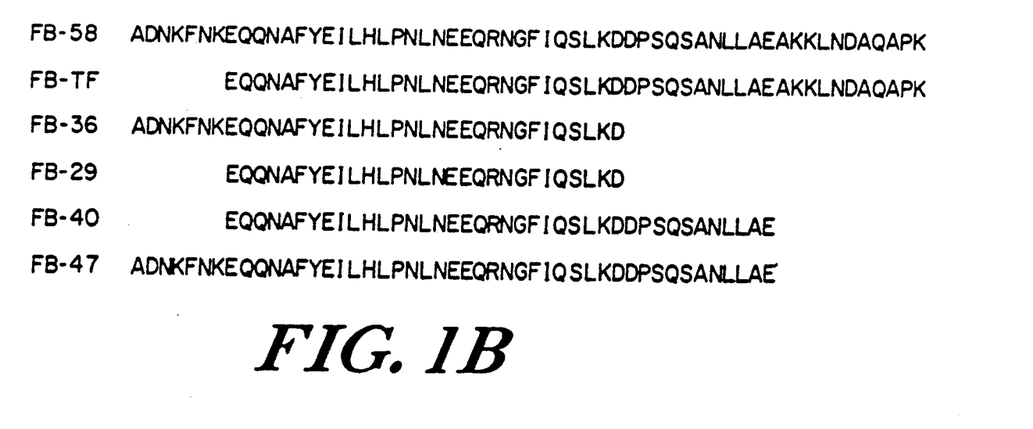
FIG. 1B is a series of protein sequences identified in single letter standard code. The protein labelled FB-58 is the same as that shown in FIG. 1A. The proteins labelled FB-TF, FB-37, FB-30, FB-40, and FB-47 illustrate exemplary truncated analogs of FB-58 having reduced Ka to the Fc region of immunoglobulin, relative to the Ka of FB-58.

The fragments of FB depicted in FIG. 1B comprise examples of such analog protein structures having fibrin binding activity. It is also contemplated that various amino acids in such sequences may be replaced while retaining significant fibrin binding activity. Other modified amino acid sequences and related sequences also may be used. These include sequences homologous to a portion of the FA, FC, FD or FE fragments of protein A, and fragments from functionally similar bacterial or other proteins such as fragments of proteins G from Streptococcus. These types of material are considered to be within the scope of the present invention and the appended claims. Such species having a relative binding affinity of 5% or more of that of the native FB peptide shown in FIG. 1 have utility. Preferably, such modified peptides have a relative binding affinity of 50% or more of the native FB fragment.

Protein A is known to bind to a site on the Fc fragment of immunoglobulin G and with many other types of human and animal immunoglobulins. Native FB and other protein A binding domains also binds with IgG, and thus IgG competes with fibrin when both are present. However, in accordance with this invention, the binding moiety can be designed to increase or retain its affinity for fibrin and to decrease its affinity for soluble immunoglobulin.

There is a binding site recognized by protein A on each of the paired heavy chain constant domains of IgG constituting the Fc region. However, steric constraints permit the native form of protein A to attach to only one site. Fibrin, on the other hand, presents an array of accessible binding sites. This structural difference is exploited to increase selectivity of the fibrin binding moiety by designing repeats or oligomers of analogs comprising adjacent binding domains, each of which individually have a relatively low affinity for Fc and fibrin. Such an oligomer has a low affinity for species comprising a single accessible binding site, such as IgG, but a higher affinity for species having multiple accessible binding sites, such as fibrin. The affinity constant of such oligomers for fibrin is higher than for IgG, and often approaches the product of the individual affinities of the repeating units. Thus, a monomeric analog having an affinity for Fc and for fibrin of, for example, $1 \times 10^3$ $M^{-1}$, can be used to produce, for example, a trimer, having an affinity for Fc of the same $1 \times 10^3$ $M^{-1}$, but an affinity for fibrin of up to $1 \times 10^9$ $M^{-1}$.

The approach used in designing such analogs having reduced fibrin binding activity, and some examples of such analogs, are illustrated in FIG. 1B. The protein labeled FB-58 is the native FB structure. FB-TF may be produced by cleaving the native form of the protein fragment with trypsin, which cleaves at the Lys7 bond FB-58 has a Ka for Fc of about $5 \times 10^7 M^{-1}$; FB-TF has a Ka for Fc of about $5 \times 10^4 M^{-1}$. The remaining analogs are made by expression of an appropriate DNA. All comprise truncated analogs of the native fragment. The approximate affinities of these analogs for Fc in liters per mole are, respectively, for FB-37, $Ka=2\times10^3$; for FB-30, $4\times10^2<Ka<2\times10^3$; for FB-40, $6\times10^3<Ka<2\times10^4$; and for FB-47, $2\times10^3$ $M^{-1}$. Oligomers of the various analogs comprise moieties having high affinity for fibrin, e.g., greater than $10^7$ $M^{-1}$ and Preferably greater than $10^8$, and low affinity for Fc, e.g., less than about $10^7$ $M^{-1}$, and preferably less than $10^5$ $M^{-1}$.

In accordance with the invention, these discoveries are exploited to provide a family of therapeutic and diagnostic reagents which may be used in vitro or intravascularly to target the locus of fibrin. The discoveries also form the basis for a process which may be used to impart fibrin affinity to a variety of biological materials. Broadly, three different classes of synthetic, fibrin-binding reagents may be produced in accordance with the invention: fibrinolytic agents; agents useful in imaging thrombi; and analgesic or therapeutic agents designed for delivery to the site of a wound. Each of these types of reagents are discussed in detail hereinafter.

The preferred approach to manufacturing the reagents exploits conventional recombinant DNA techniques wherein recombinant DNA encoding a fused polypeptide is inserted into a suitable host cell, and the resulting protein is expressed, harvested, renatured if necessary, and purified. The fused polypeptide comprises the fibrin binding domain linked to a biologically active domain having analgesic, therapeutic, or fibrinolytic activity, to a polypeptide backbone useful as a site for attachment of such an agent, or linked to a site for attachments of a remotely detectable moiety such as a gamma emitting atom.

The processes for manipulating, amplifying, and recombining DNA which encode amino acid sequences of interest are generally well known in the art, and therefore, disclosed only in summary form herein. Methods of identifying and isolating genes encoding particular proteins, or for constructing such genes, are well understood and developed. These processes are described in the patent and other literature, and in general, involve selecting genetic material coding for amino acids which define the polypeptide of interest according to the genetic code.

The DNA constructs and fused polypeptides discussed herein can be manufactured using such known construction techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short oligonucleotides, cDNA synthesis techniques, and synthetic probes for isolating genes having a particular function. Machines capable of automatic synthesis of relatively lengthy oligonucleotides of any desired sequence are available commercially. These oligonucleotides can be ligated to form double stranded DNA, and the DNA can be amplified, incorporated into an expression vector, and expressed in various hosts. Various promoter sequences and other regulatory DNA sequences used in achieving expression, and various types of host cells are also known and available. Conventional transfection techniques, and equally conventional techniques for cloning and subcloning DNA are also useful in the practice of this invention and known to those skilled in the art. Various types of vectors may be used such as plasmids and viruses including animal viruses and bacteriophages. The vectors may exploit various marker genes which impart to a successfully transformed cell a detectable phenotypic property that can be used to identify which of a family of cells has successfully incorporated the recombinant DNA of the vector.

The reagents and process of the invention also may be practiced using protein synthesis techniques and organic chemistry not involving expression of DNA.

The fibrinolytic agents that can be produced in accordance with the invention have the general formula $(F)_n$-L-I, where F is a fragment of protein A, e.g., FB, or an analog thereof which retains fibrin binding ability, n is an integer, preferably from 1-10, L is a bond such as a peptide bond or an amino acid sequence or other linking moiety, and I is a polypeptide comprising the catalytic fragment of, e.g., urokinase, streptokinase, or a tissue plasminogen activator. The full length DNA sequence of two embodiments of these reagents, as well as the amino acid sequence of each, are set forth, respectively, in FIGS. 3 and 5A and 5B.

In FIG. 3, depicting the UK conjugate, the binding domain is an FB—FB dimer whose amino acid sequence begins at the Ala, Asp, Asn residues (bases 10-18), extends through the Ala, Pro, Lys residues (bases 176-184) and then repeats (bases 185-358). In

Figure 3A:
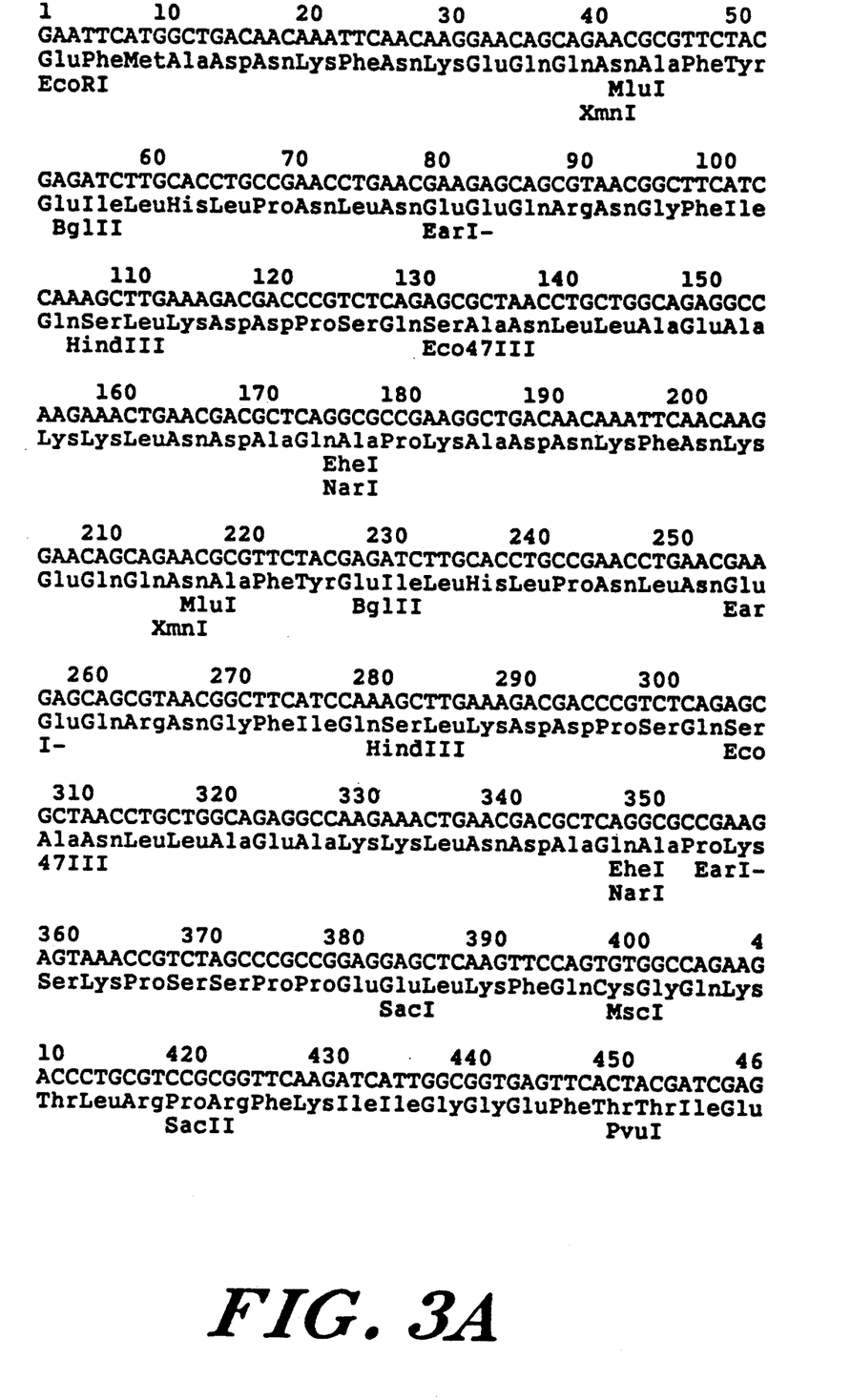
FIG. 3 is the full length DNA sequence of the catalytically active fragment of urokinase (and prourokinase), connected through DNA encoding a linker sequence and DNA encoding an FB fragment dimer, together with the amino acid sequence specified by the DNA.
Figure 5A:
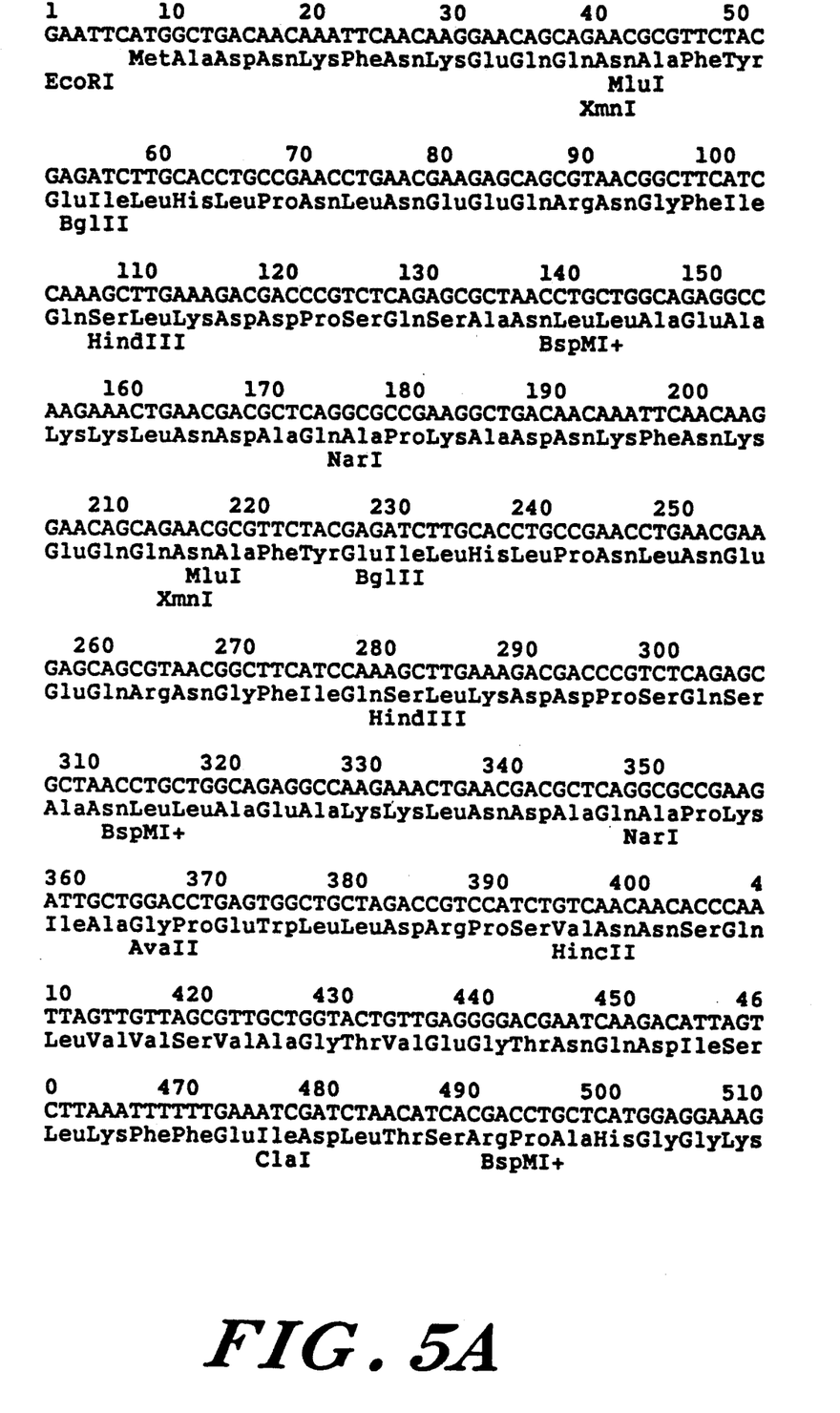
FIGS. 5A and 5B are the full length DNA sequence of the catalytically active fragment of streptokinase connected through DNA encoding a linker sequence and DNA encoding an FB fragment dimer, together with the amino acid sequence specified by the DNA.
Figure 5B:
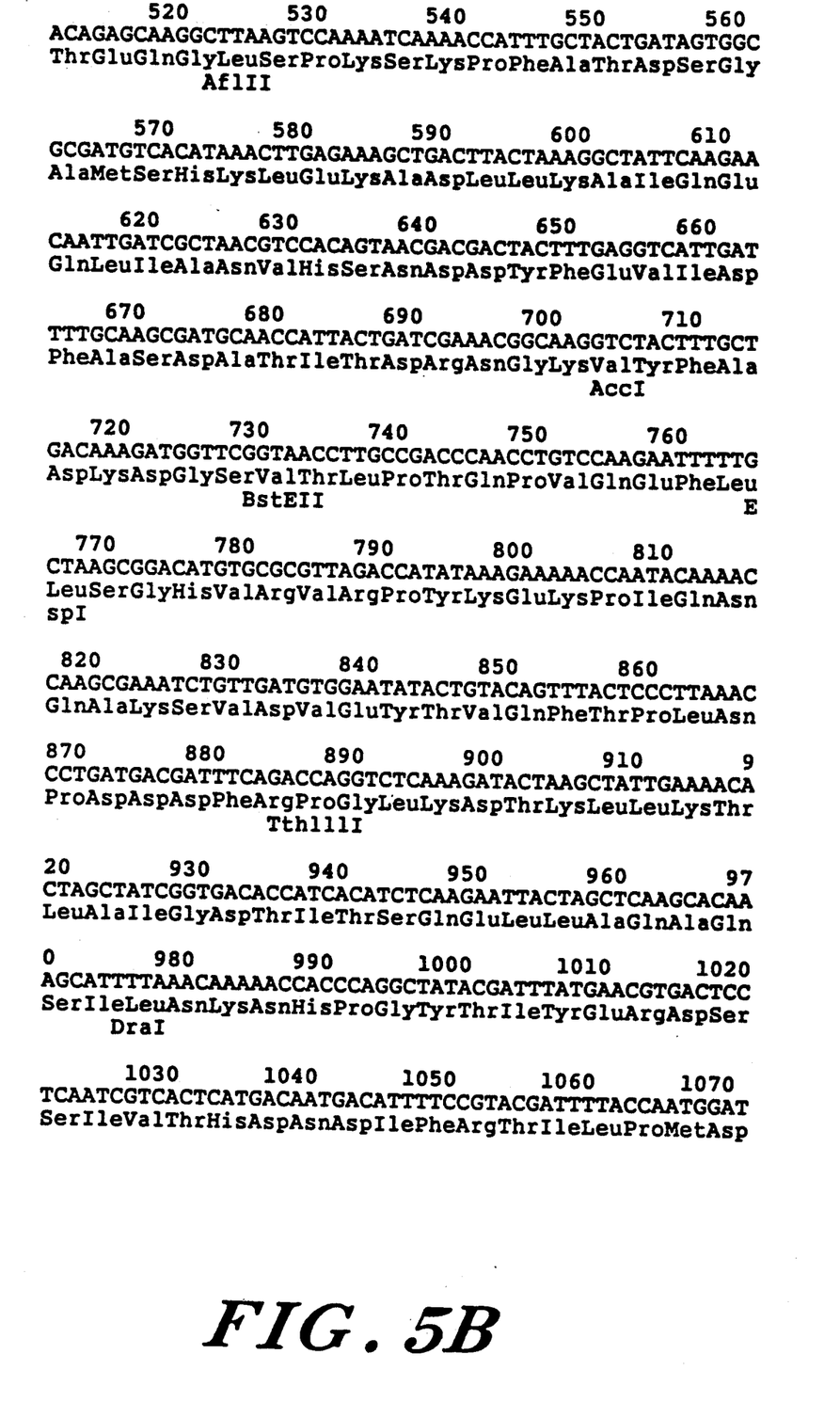
Figure 5C:
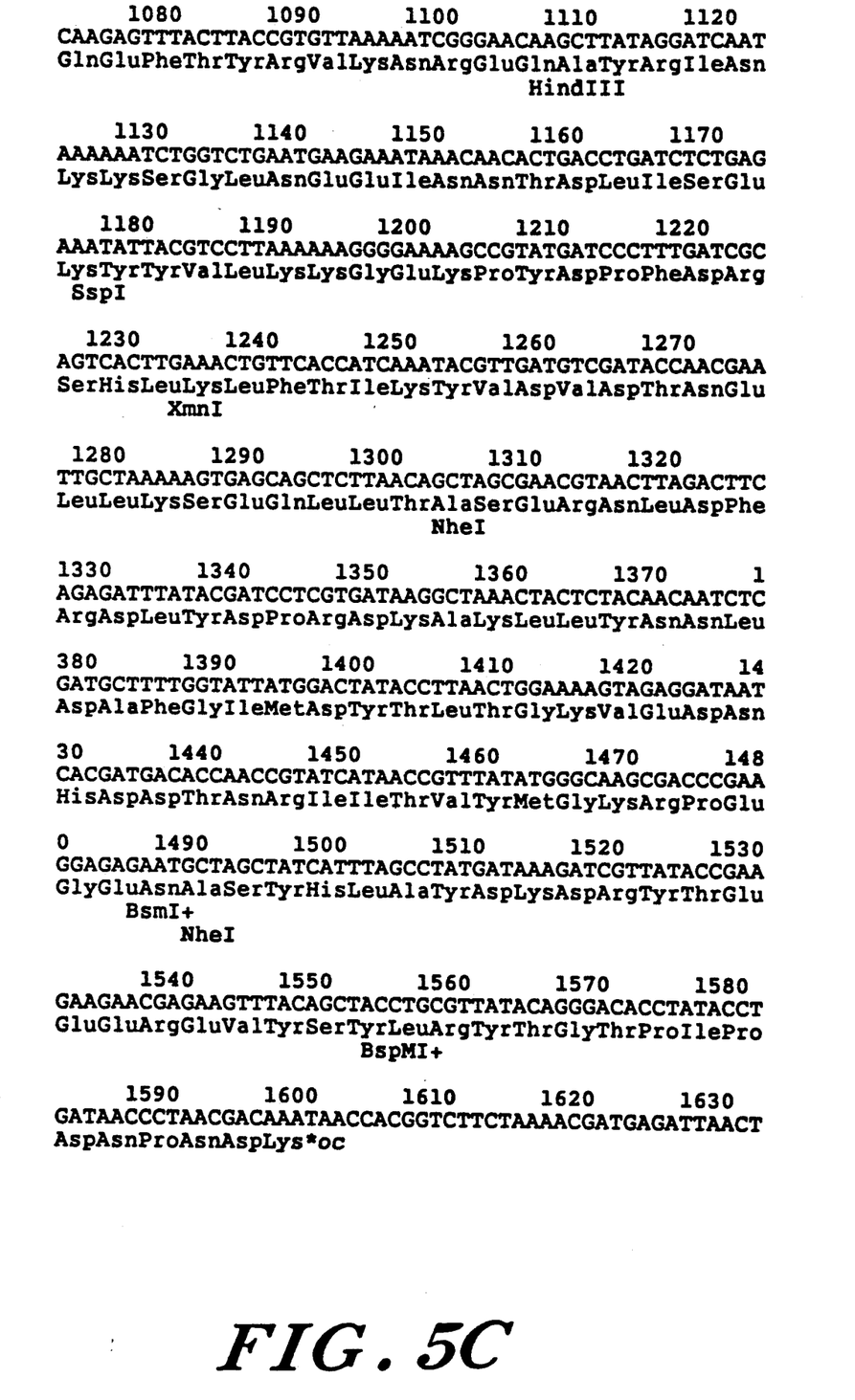
Figure 5D:
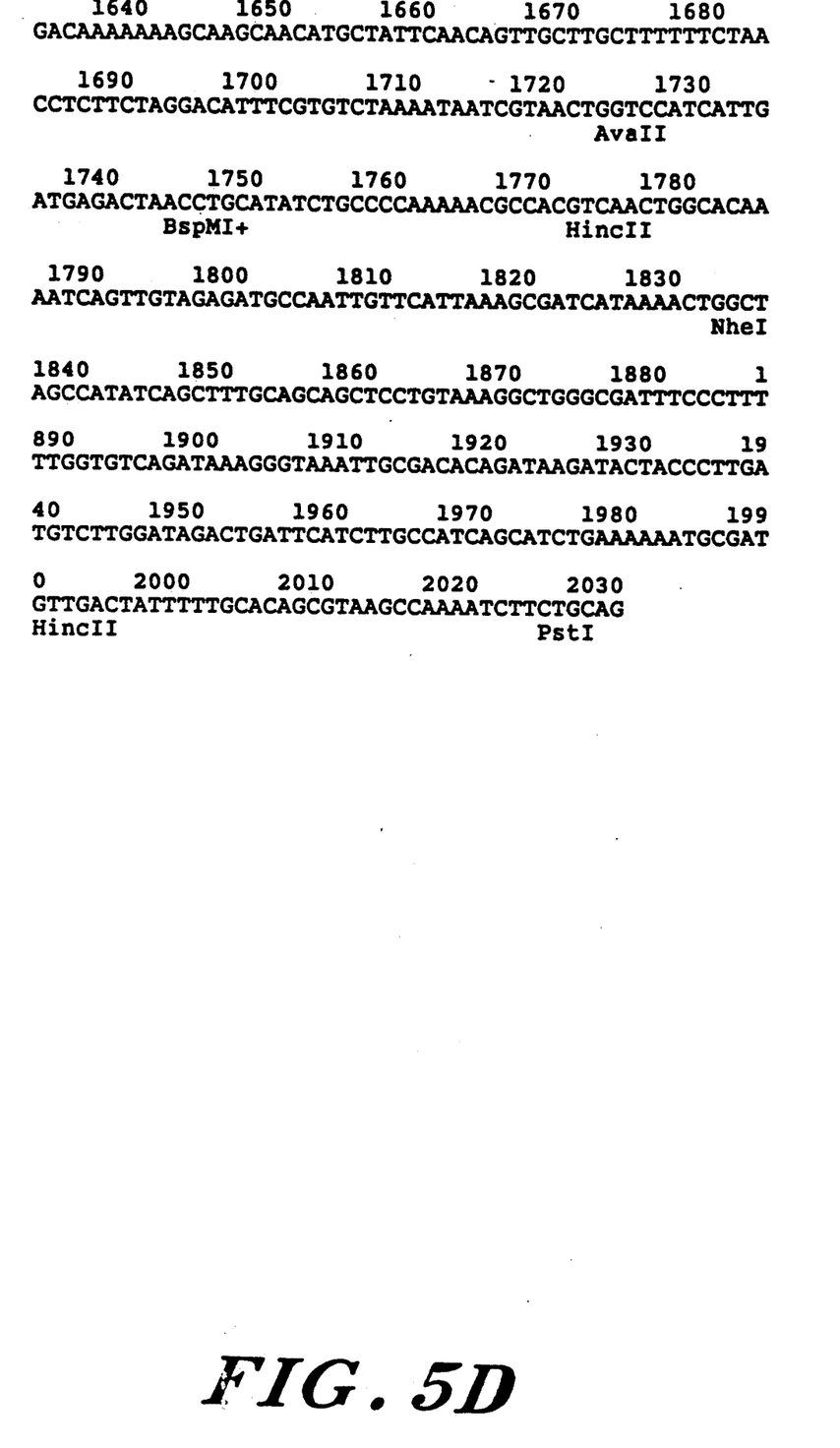

FIG. 5A and 5B, depicting the FB-FB-SK conjugate, the binding domain is identical (amino acids corresponding to bases 10-358). The UK conjugate of FIG. 3 has a Ser residue as a linking group, followed by the sequence comprising the DNA and amino acids defining the B chain of human urokinase (bases 362-1195). The SK conjugate of FIG. 5A and 5B has a peptide bond disposed between the last amino acid of the binding domain (Lys) and the first amino acid of the sequence defining the streptokinase (amino acids corresponding to bases 359-1601).

Oligomers comprising repeats of lower binding analogs of the type described above may be used in place of the FB-FB dimer to produce a family of constructs having increased affinity for fibrin relative to the native FB form and/or decreased affinity for Fc. In view of this disclosure those skilled in the art can produce other sequences which function to target fibrin, derived from bacterial proteins such as protein A and protein G, which thus comprise analogs of FB, as that phrase is used herein. Other non-limiting examples of equivalent targeting moieties include analogs produced by deleting some fraction of the native amino acid sequence of FB or other fragments of protein A, and/or replacing selected amino acids with others, and proteins comprising plural binding sites of this type. Of course, each of the individual binding sites need not be identical.

The linking segment may comprise a Polypeptide such as a relaxed, unstructured segment which permits the binding domain and catalytic fragment to assume independently their native conformation. Such polypeptide linkers provide one method of assuring that the fused protein as expressed contains both fibrin binding ability and fibrinolytic activity. The linker may be omitted altogether. However, it is preferred that such a polypeptide linker, if used, be free of cysteine residues, contain one or more proline residues which prevent the formation of a structured alpha helix, and contain charged or hydrophilic amino acid residues such as GLU ASP ARG LYS and THR to promote solubility of the linker region.

When labelled with a suitable radioisotope the fibrin binding proteins enable detection of the locus of a thrombus by external detection of emitted radiation. Suitable radioisotopes are well known and include $^{125}I$, $^{131}I$, $^{99}Tc$, $^{111}In$, and $^{77}Br$. Radioactive gamma emitters are preferred, although in some circumstances positron emitters, such as $^{64}Cu$, $^{11}C$, and $^{15}O$ may be used. It is also contemplated that the fibrin binding proteins may be labelled with a paramagnetic substance such as gadolinium so that concentrations of the reagent localized about a thrombus may be imaged by nuclear magnetic resonance imaging techniques.

The proteins of the invention can be labelled with such agents using conventional techniques used to label other proteins known to those skilled in the art. The currently preferred technique is to express a fused polypeptide comprising the fibrin binding domain and, covalently linked on either its 3' or 5' end, a lysine rich polypeptide sequence comprising, for example, 2-20 residues, to serve as a site of attachment for the remotely detectable moieties discussed above. The gamma or positron emitting ions are preferably attached to these linkers by ionic interaction or chelation with the free amine groups on the lysine residues.

For example, diethylenetriamine penta acetic acid (DTPA) may be used to label with Tc-99 or In-111. In or I isotopes may be attached using the oxine salt (8-hydroxy quinoline). Iodogen (1, 3, 4, 6 tetrachloro - 3α,6α diphenylglucoluril - Pierce Chem. Co, Roskville, Ill.) may be used for labeling with $^{125}I$. See, e.g., Thakur et al. Thromb. Res. 9:345 (1976); McFarlane, J. Clin. Invest. 42:346 (1963); Knight et al, Radiopharmaceuticals, N.Y. Soc. of Nuclear Medicine, 1975, pp 149; and Harwig et al, Int J. Appl Radiat Isot 27:5, 1976. Other methods are known to those skilled in the art.

In view of the foregoing, it will be apparent that other types of known reagents can be linked using conventional techniques to the fibrin binding domain to impart to those reagents an affinity for fibrin. Examples include therapeutic drugs which promote healings such as calcitonin, epidermal growth factor, tumor growth factor alpha and beta, platelet derived growth factor, insulin-like growth factor 1 (Somatomedin-C), connective tissue activating peptide, and human collagenase inhibitor. When conjugates with the fibrin binding domain disclosed herein are injected, they accumulate at the site of a wound where fibrin is present.

The dosage and means of administration of the family of fibrin specific agents constructed in accordance with the invention will necessarily depend on the nature of the drug involved, the degree if any that its bioactivity is reduced when it is present as a conjugate, the immunological tolerance of specific patients, and the nature of the diseased condition in question. When the polypeptide is linked to an imaging agent, it should be administered in an amount sufficient to be detected by scintillation scanning or other external radiation detection means capable of detecting the localized radiation present in the thrombus, such as autoradiography. In general, about 5-20 microcuries should be administered; most preferably about 10 microcuries. The actual amount depends on the location of the thrombus as is well known in the art. Additional radioactive peptide may be injected if necessary up to the amounts limited by prevalent standards of safety.

It is contemplated that administration of any of the drugs of the invention be conducted by intravascular or intramuscular injection or other means which avoids gastric digestion.

The invention will be further understood from the following non-limiting examples.

EXAMPLES

The nucleotide sequence set forth in FIG. 1A, and DNAs encoding any of the constructs illustrated in FIGS. 1B, 3, or 5A and 5B, may be synthesized chemically by the phosphotriester method of Crea and Horn (Nucl. Acid Res. V 8, p. 2331, 1980). This involves in situ preparation of phosphoramidites, oligonucleotide synthesis using, e.g., an automated, commercially available oligonucleotide synthesizer, and enzymatic ligation using, e.g., T4 DNA ligase. The DNA fragments may be resolved by electrophoresis, and extracted and precipitated with absolute ethanol. The synthetic gene may be designed to include sticky ends and to be inserted into suitable plasmids used to transform *E. coli* or other types of cells. Selection may be conducted in the presence of ampicillin or other selective toxin, and the purified plasmids may be screened by polyacrylamide gel electrophoresis after restriction digestion. After DNA sequence analysis to verify the correct gene sequence, expression vectors producing large amounts of the protein may be constructed and transfected into any of a large number of host cells. The transfectants may be fermented to produce the protein species in abundance.

Preferably, any additional protein domain in the conjugate is engineered at the DNA level, and a fusion protein is expressed which utilizes the FB or FB-like fibrin binding protein as the leader. The cell paste containing inclusion bodies are washed with detergent to remove contaminating protein, incubated on ice, centrifuged, and treated with aprotinin to inhibit protease activity. The protein is extracted from the inclusion body preparation by sequential resuspensions, denatured, and then renatured in buffer containing EDTA, a detergent, one mM reduced glutathione, and 0.1 mM oxidized glutathione. The detergent and renaturant are removed by dialysis.

The FB fragment protein having the sequence shown in FIG. 1A was purified by HPLC and then labelled with $^{125}I$ to test its ability to bind to fibrin.

Iodination of FB monomer expressed from the synthetic gene of FIG. 1A in *E. coli* strain K12 JM-83 (ATCC No. 35607) was carried out by the Chloramine T method (Hunter et al, Preparation of Iodine 131 Labelled Human Growth Hormone of High Specific Activity, Nature, 194: 495–496, 1962). 100 microliters of the FB fragment (1 mg. per ml.) is diluted with 100 microliters of 0.5M phosphate buffer, pH 7.5, in a 1.5 ml centrifuge tube. 10 microliters of 0.5 to 1.0 mC of I(125) and 50 microliters of the chloramine T solution (5 mg per ml in 0.05M phosphate buffer, pH 7.5) are added. The solution is immediately stirred on a vortex. After 1 minute of incubation, the reaction is stopped by adding 200 microliters of sodium metasulphite solution (2.4 mg per ml in 0.05M phosphate buffer, pH 7.5). To remove the unbound I(125), the solution is allowed to pass through a Dowex column, equilibrated with 0.05M phosphate buffer, pH 7.5, containing 0.15M sodium chloride. The unbound labelled protein is then washed out of the column with 600 microliters of 0.05M phosphate buffer, pH 7.5, containing 0.15M sodium chloride. The protein solution, approximately 1 ml, is mixed with equal volume of phosphate buffered saline, pH 7.5, containing 3% bovine serine albumin and 0.1% sodium azide. The solution is then stored at 4 C.

This method may be adapted to synthesize radiation-emitting thrombus imaging agents constructed in accordance with the invention.

Fibrinogen was placed in the wells of a microtiter plate and subsequently treated with thrombin to produce fibrin. Test wells were left uncoated or coated with bovine serum albumin. The labeled FB dissolved in phosphate buffered saline was added to each of the wells in various concentrations and incubated at 37° C. for two hours to promote binding. After incubation, the supernatants were removed, and the wells were washed with 100 microliters phosphate buffered saline. The amount of bound and unbound fragment were determined by detecting gamma emissions in the respective wells using a gamma counter. It was found that more than six times as much FB bound to the fibrin coated wells as compared with uncoated wells, and that the wells containing bovine serum albumin contained even lower levels of the labeled fragment than the untreated wells.

Figure 2:
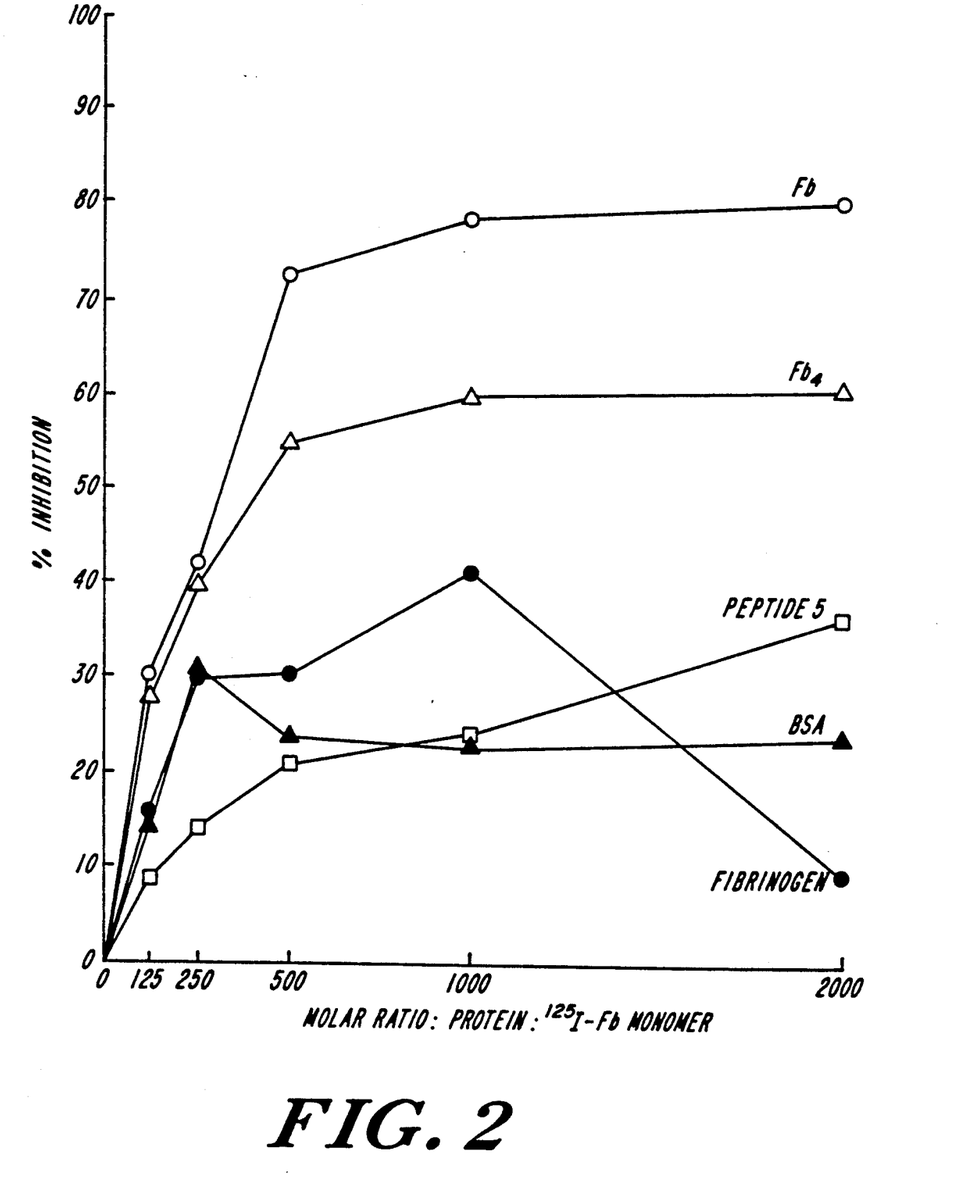
FIG. 2 is a graphic representation of the results of an FB-fibrin binding inhibition assay illustrating the specificity of the protein A fragment of FIG. 1A for fibrin.

A separate experiment measured the relative ability of bovine serum albumin (BSA), peptide 5 (trypsin digest product of FB or FB-TF,) fibrinogen, FB monomer, and FB tetramer to compete with I-125 labelled FB monomer binding to fibrin-containing plates. The results are shown in FIG. 2. As illustrated, the decreasing order of inhibition of binding is (1) monomer, (2) FB tetramer, (3) peptide 5, BSA, and (5) fibrinogen. The observation that FB I 125 monomer binds equally well to both thrombin treated and non-thrombin treated fibrinogen coated wells, but that soluble fibrinogen competes poorly, suggests that the coating and drying process of the fibrinogen enhances in some manner the bonding of FB I-125 monomer to fibrinogen immobilized on the solid phase. In addition, FB-58 was shown not to bind to bovine serum albumin. Since fibrinogen and BSA have comparable inhibition characteristics (FIG. 2), this observation supports the hypothesis that FB-58 has a higher affinity for fibrin than for fibrinogen.

EXAMPLE 2

Figure 3B:
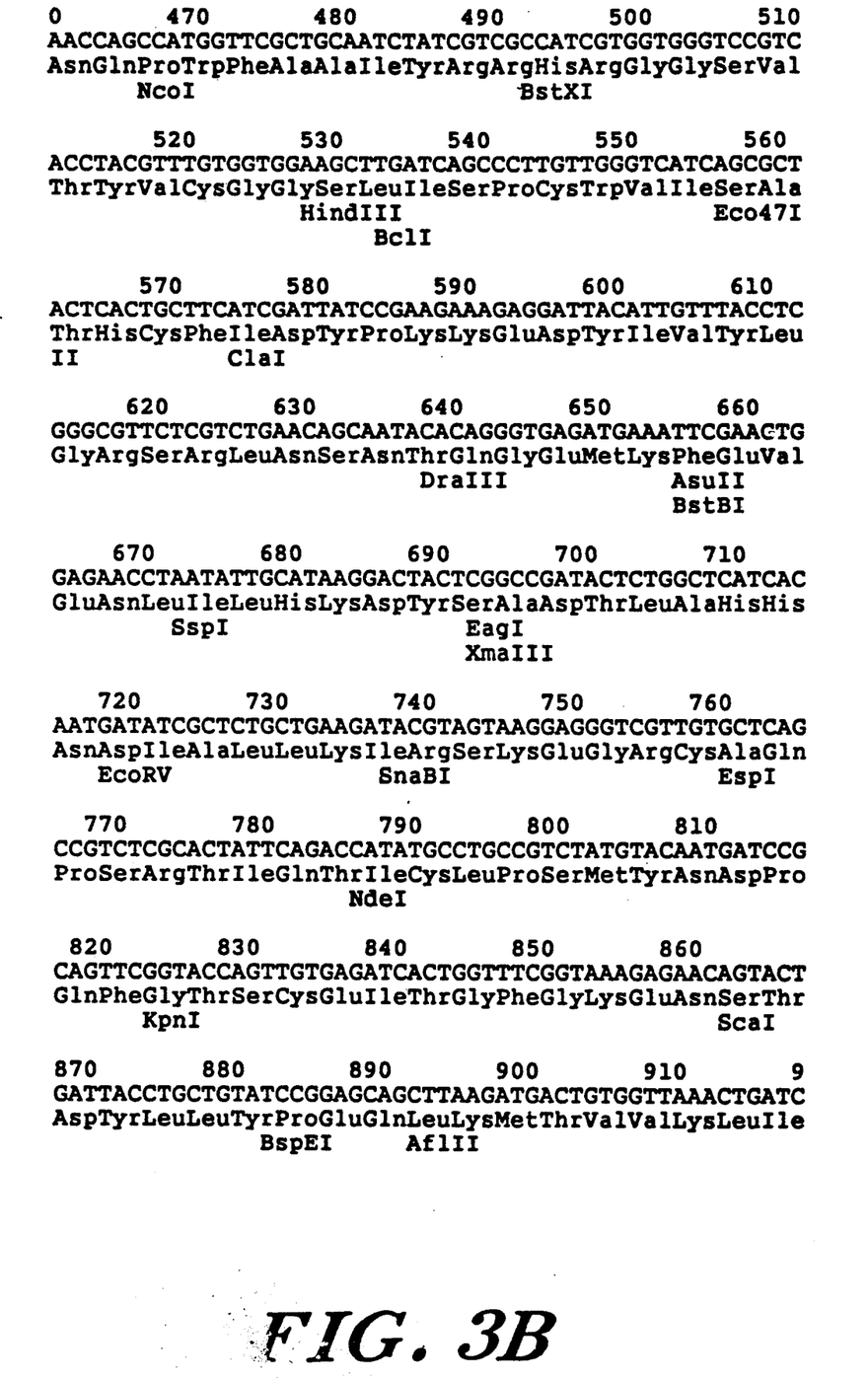
Figure 3C:
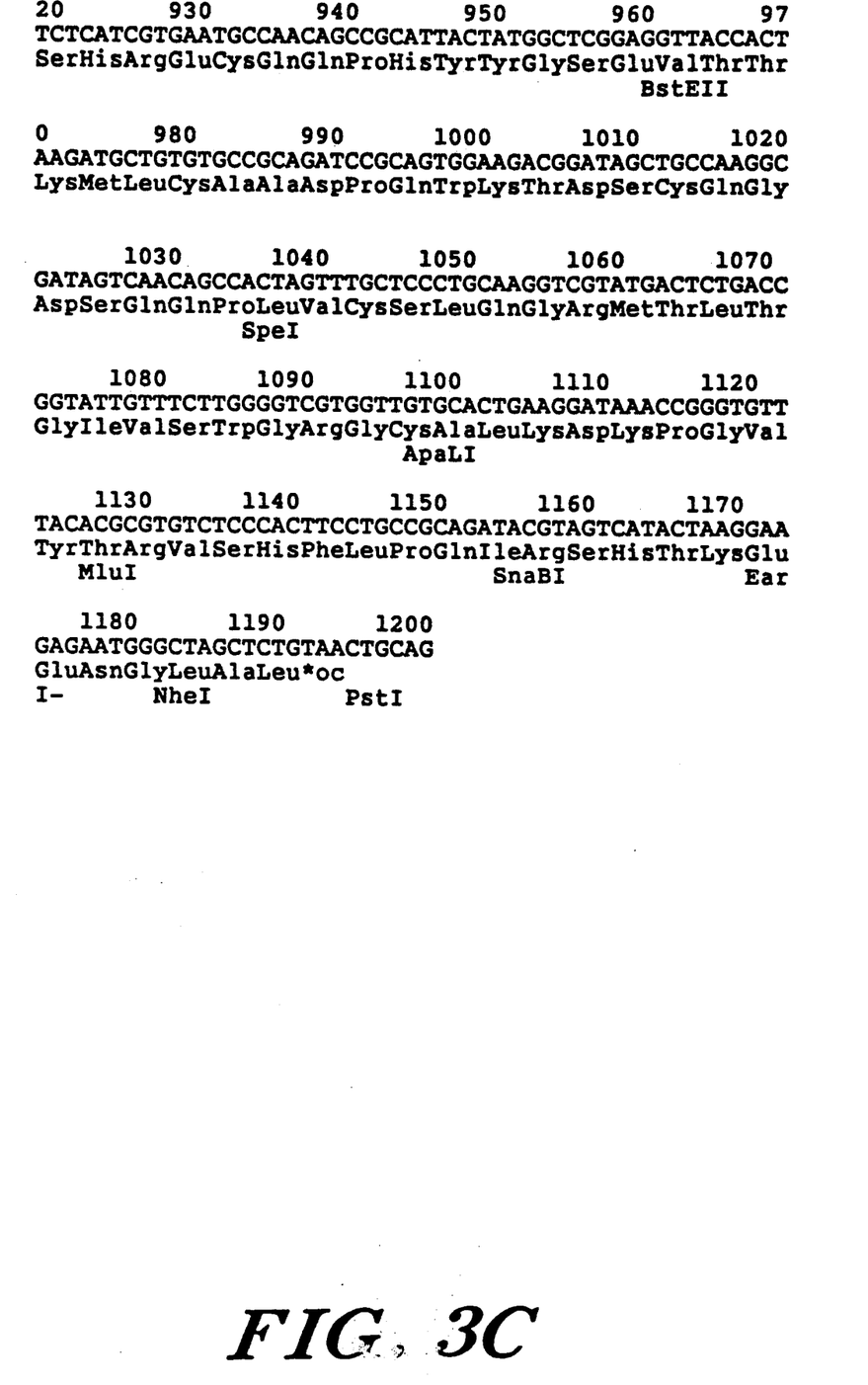
Figure 4:
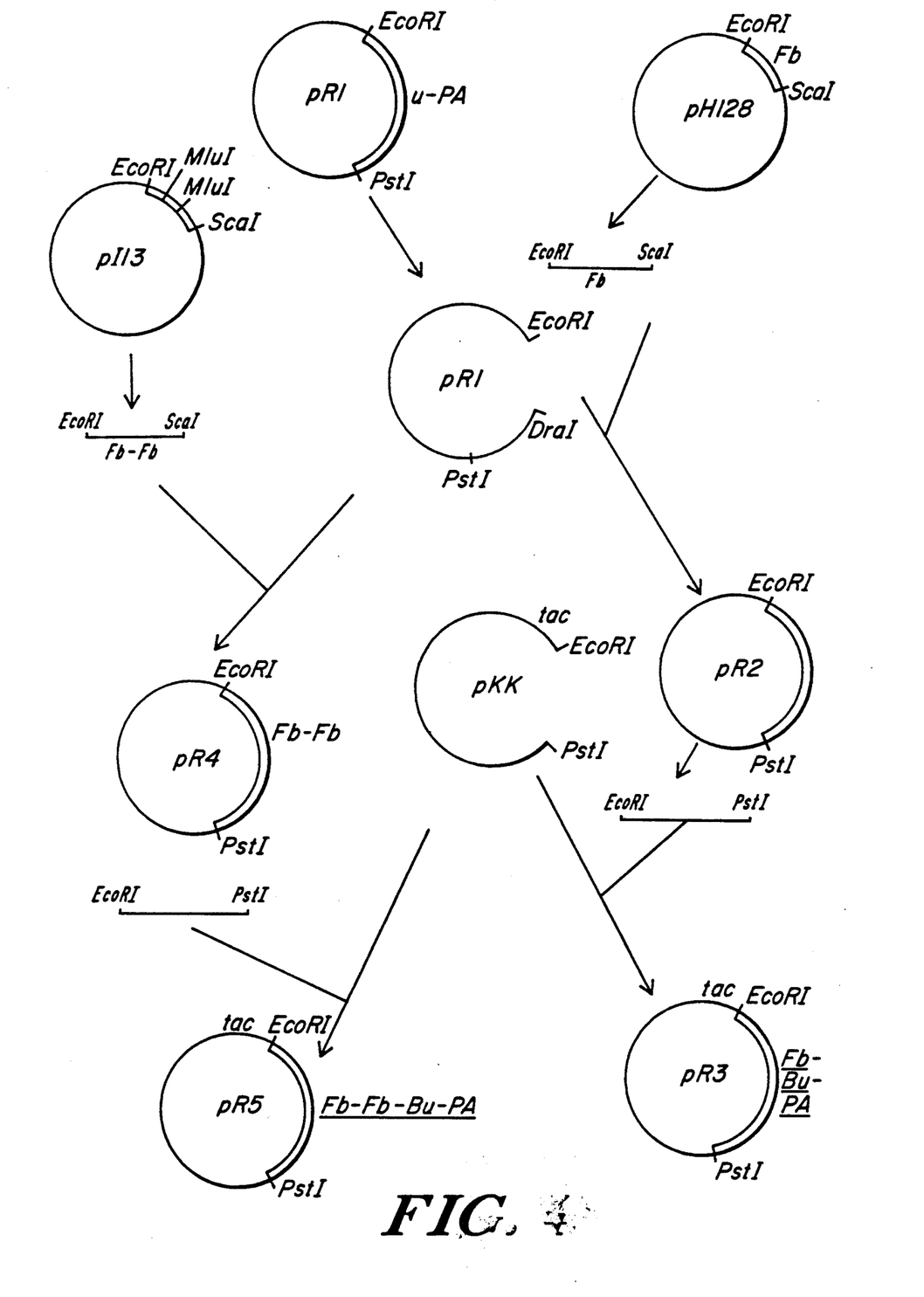
FIG. 4 is a diagram illustrating a method of constructing the DNA sequence of FIG. 3.

The conjugate of FIG. 3, comprising a fibrin binding domain consisting of an FB dimer linked through a serine residue to the catalytically active site of urokinase (beta chain), may be produced using established genetic engineering techniques. One such technique is depicted in FIG. 4.

Plasmid pR1 is first synthesized from plasmid DNA and, for example, a synthetic gene encoding the entirety of the sequence of prourokinase flanked by EcoR1 and PstI restriction sites. The FB Protein, isolated in a vector such as is discussed in Example 1, here named pH128, and flanked by EcoR1 and ScaI restriction sites, is used as the binding domain. Plasmid pRI is restricted with EcoR1 and DraI to remove the 5' portion of the prourokinase gene, leaving a segment corresponding to a portion of the DNA sequence of FIG. 3 defining the UK catalytically active fragment flanked by a PstI cleavage site and a DraI blunt end. DNA encoding the FB protein having an EcoRI sticky end and a blunt end, e.g., ScaI, is inserted into pRI to produce pR2, a plasmid harboring DNA encoding an FB-UK conjugate, or plasmid pR4 harboring DNA encoding an FB-FB-UK conjugate. DNA flanked by the sticky EcoRI site and blunt ScaI end and encoding the FB-FB dimer having the sequence set forth in FIG. 3 may be maintained in a plasmid, here designated pI13, produced by ligating DNA derived from assembled synthetic oligonucleotides in any suitable replicable vector.

Either DNA may be expressed by transfer to an expressing vector, here pKK, (Brosius et al, Proc. Natl. Acad. Sun, 81:6929, 1984), having a suitable Promoter and other regulatory sequences, by restricting pR4 or pR2 with Eco RI and Pst 1, and ligating the restriction fragment into plasmid pKK. The resulting expression plasmids, here designated pR5 and pR3, are used to transform a suitable host cell, e.g., an *E. coli* strain.

The conjugates are produced as inclusion bodies which are collected and purified using known techniques.

EXAMPLE 3

Figure 6:
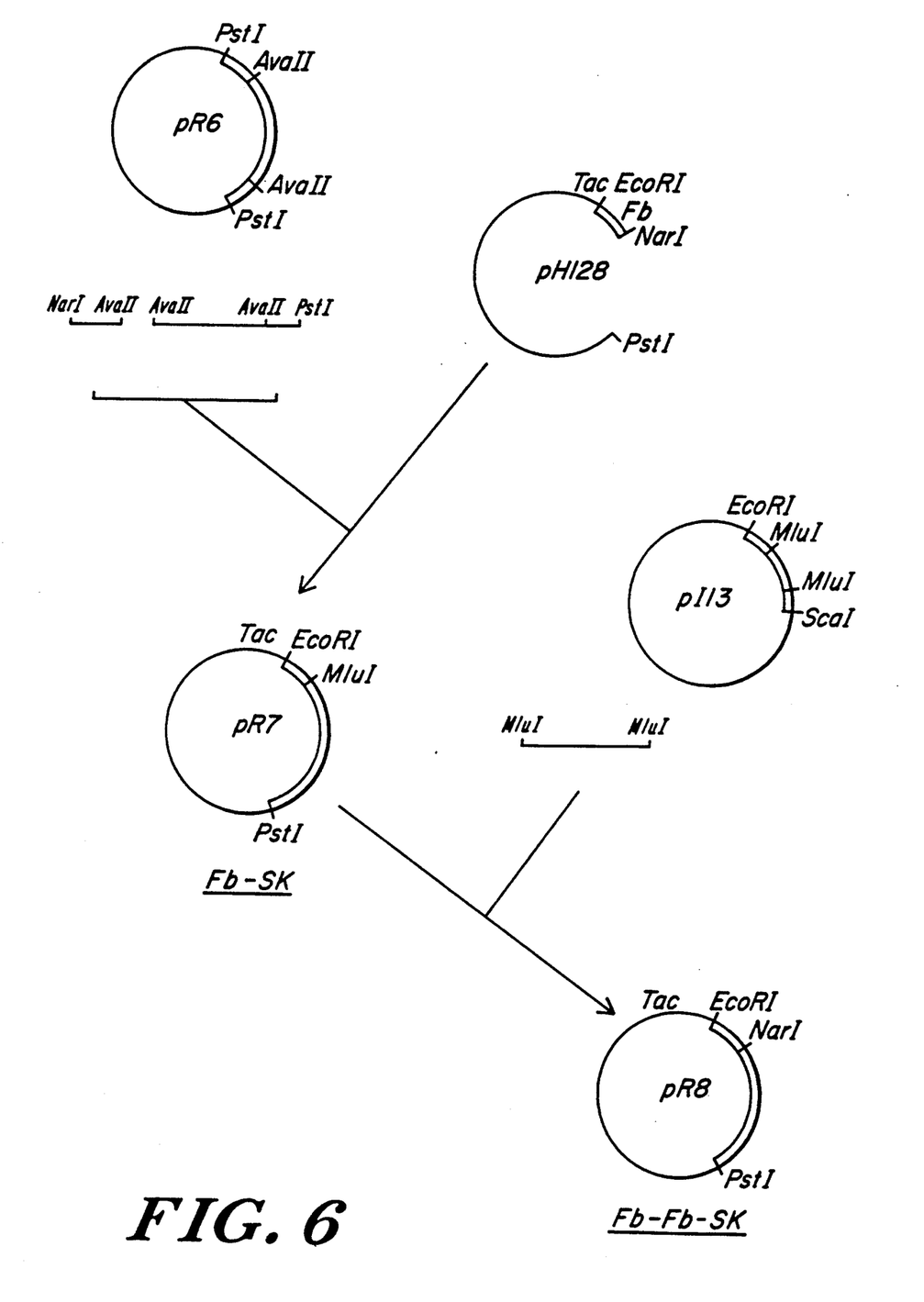
FIG. 6 is a diagram illustrating a method of constructing the DNA sequence of FIGS. 5A and 5B.

The conjugate of FIG. 5A and 5B, comprising FB dimer and streptokinase linked together directly may be produced as depicted in FIG. 6.

A 2568-bp PstI fragment from the genome of *Streptococcus equisimilis* H46A encoding the streptokinase gene (SK) is cloned into pBR322 to form pR6 (Malke et al, Proc. Natl. Acad. Sci., 81:3557, 1984). An AvaII to PstI fragment, isolated from pR6, and a synthetic NarI to AvaII linker, are cloned into pH128 (see previous example), opened at the NarI and PstI sites, to produce plasmid pR7. This plasmid may be used to produce a synthetic fibrinolytic agent comprising FB-SK in *E. coli*. To express the streptokinase fragment having the FB dimer as the leader, a MluI fragment, isolated from pI13 (see previous example), is cloned into pR7 at the MluI site to form pR8. The effect of restricting PI13 with MluI is to cut the DNA of both tandem FB encoding sequences at the unique MluI site, producing a fragment consisting of trailing nucleotides of the first FB and leading nucleotides of the second FB (see FIG. 3A). Ligation of this fragment into the MluI site in pR7 produces pR8. The effect of restricting PI13 with MluI is to cut the DNA of both tandem FB encoding sequences at the unique MluI site, producing a fragment consisting of trailing nucleotides of the first FB and leading nucleotides of the second FB (see FIG. 3A). Ligation of this fragment into the MluI site in pR7 produces pR8.

The invention may be embodied in other specific forms. Accordingly, other embodiments are within the following claims.

What is claimed is:

1. A method for imparting to an injectable reagent an affinity for an intravascular thrombus, said method comprising the step of linking to said injectable reagent a fibrin binding domain comprising a protein having an affinity for fibrin and a sequence identical or homologous to the FA, FB, FC, FD, or FE fragments of protein A or portion thereof, a protein analog thereof having at least about 5% to 50% of the fibrin affinity of fragment B of Protein A, or an oligomer of the protein or the protein analog.

2. The method of claim 1 wherein the oligomer of said protein or said protein analog comprises 2–5 repeats of the protein or protein analog.

3. The method of claim 1 wherein said fragment of Protein A comprises the FB binding domain fragment.

4. The method of claim 1 wherein said protein comprises the amino acid sequence:

MADNKFNKEQQN
AFYEILHLPNLN
EEQRNGFIQSLK
DDPSQSANLLAE
AKKLNDAQAPK or a portion thereof having residual fibrin affinity.

5. The method of claim 1 wherein said protein comprises an oligomer comprising at least two of said fibrin binding analogs, each one of which has an affinity constant Ka for the Fc portion of immunoglobulin less than about $10^7 M^{-1}$, and wherein said protein has an affinity constant Ka for fibrin of at least $10^8 M^{-1}$.

6. The method of claim 5 wherein each of said fibrin binding analogs has an affinity constant Ka for the Fc portion of immunoglobulin less than $10^5 M^{-1}$.

7. A method of imparting to an injectable reagent an affinity for an intravascular thrombus, the method comprising the step of linking to the injectable reagent a fibrin-binding fragment B (FB) of protein A, a fibrin-binding portion thereof or an oligomer thereof.

8. A method of claim 7, wherein the fragment B of protein A has the amino acid sequence:

MADNKFNKEQQN
AFYEILHLPNLN
EEQRNGFIQSLK
DDPSQSANLLAE
AKKLNDAQAPK or a fibrin-binding portion theerof.

9. A method of claim 7, wherien an FB-Fb dimer is linked to the reagent.

10. A method of claim 7, wherein the injectable reagent is a fibrinolytic agent.

11. A method of claim 7, wherein the fibrinolytic reagent is selected from the group consisting of urokinase and streptokinase.

* * * * *